US009575302B2

(12) United States Patent
Booth et al.

(10) Patent No.: US 9,575,302 B2
(45) Date of Patent: Feb. 21, 2017

(54) STIMULATED EMISSION DEPLETION MICROSCOPY (71) Applicant: ISIS Innovation Limited, Oxfordshire (GB)

(72) Inventors: Martin Booth, Oxfordshire (GB); Daniel Burke, Oxfordshire (GB); Joerg Bewersdorf, New Haven, CT (US); Travis J. Gould, New Haven, CT (US)

(73) Assignee: ISIS Innovation Ltd, Oxfordshire (GB)

(*) Notice: Subject to any disclaimer, the term of this patent is extended or adjusted under 35 U.S.C. 154(b) by 0 days.

(21) Appl. No.: 14/423,188

(22) PCT Filed: Aug. 16, 2013

(86) PCT No.: PCT/GB2013/052183
§ 371 (c)(1),
(2) Date: Feb. 23, 2015

(87) PCT Pub. No.: WO2014/029978
PCT Pub. Date: Feb. 27, 2014

(65) Prior Publication Data
US 2015/0226950 A1 Aug. 13, 2015

Related U.S. Application Data (60) Provisional application No. 61/692,367, filed on Aug. 23, 2012.

(30) Foreign Application Priority Data

Sep. 26, 2012 (GB) .................... 1217171.6

(51) Int. Cl.
G01J 1/58 (2006.01)
G02B 21/00 (2006.01)
(Continued)

(52) U.S. Cl.
CPC ......... *G02B 21/0072* (2013.01); *G01N 21/636* (2013.01); *G01N 21/6456* (2013.01);
(Continued)

(58) Field of Classification Search
CPC G01N 21/6428; G01N 21/6458; G01N 21/64; G01N 21/6408; G01N 2021/6421
See application file for complete search history.

(56) References Cited

U.S. PATENT DOCUMENTS

2008/0018891 A1* 1/2008 Hell .................. G01N 21/6458
356/317

OTHER PUBLICATIONS

Rueckel et al. "Adaptive wavefront correction in two-photon microscopy using coherence-gated wavefront sensing", Proceedings of the National Academy of Sciences, vol. 103, No. 46, Nov. 14, 2006 pp. 17137-17142, XP055090562.*
(Continued)

*Primary Examiner* — David Porta
*Assistant Examiner* — Mamadou Faye
(74) *Attorney, Agent, or Firm* — Wood, Phillips, Katz, Clark & Mortimer (57) ABSTRACT Aberrations in stimulated emission depletion microscopy are corrected using an adaptive optics approach using a metric which combines both image sharpness and brightness. Light modulators (22,32) are used to perform aberration correction in one or more of the depletion path (10), the excitation path (12), or the emission path from sample to detector.

19 Claims, 4 Drawing Sheets (51) Int. Cl.
*G02B 26/06* (2006.01)
*G01N 21/63* (2006.01)
*G01N 21/64* (2006.01)

(52) U.S. Cl.
CPC ..... *G01N 21/6458* (2013.01); *G02B 21/0076* (2013.01); *G02B 26/06* (2013.01)

(56) References Cited

OTHER PUBLICATIONS

Auksorius et al. "Stimulated emission depletion microscopy with supercontinuum source and fluorescence lifetime imaging", Optics letters, vol. 33, No. 2, Jan. 1, 2008 p. 113-115 XP55090361.*
Gould et al. "Total internal reflection STED microscopy", Optics Express, vol. 19, No. 14, Jul. 4, 2011 pp. 13351-13357, XP55090255.*
Image Analysis.*

\* cited by examiner

STIMULATED EMISSION DEPLETION MICROSCOPY

SPONSORED RESEARCH OR DEVELOPMENT

The invention was made with government support under GM096859 awarded by National Institutes of Health. The government has certain rights in the invention.

FIELD OF INVENTION

The invention relates to a method of stimulated emission depletion microscopy, computer program code for such a method and a stimulated emission depletion microscope.

RELATED ART

Stimulated emission depletion (STED) microscopy is used to image both thin samples such as single cells but also thick samples such as tissue sections, nematodes or even living mice. The technique is a fluorescence microscopy technique.

STED microscopy overcomes the diffraction limit by superimposing a conventional excitation focus with a second laser focus of high intensity—the depletion-focus—which is red-shifted with regard to the peak of the fluorescence spectrum and features a central intensity minimum (ideally an intensity zero). The depletion laser forces excited fluorophores back to the ground state by stimulated emission and thereby suppresses fluorescence at the periphery of the excitation focus, leaving only fluorescence in a very small central intensity minimum to be imaged. Increasing the intensity of the depletion beam reduces the effective point spread function (PSF) to a size that is in principle diffraction-unlimited.

In practice, the obtainable resolution in STED microscopy depends strongly on the quality of the intensity minimum in the center of the depletion focus: for non-negligible minimum intensities, fluorescence is also depleted in the center of the focus and resolution improvement is countered. Both system- and sample-induced aberrations of the depletion laser beam can dramatically decrease the beam quality and create non-negligible minimum intensities. STED microscopy deep in aberrating samples is therefore far from trivial.

A most commonly used depletion profile, which is created by a helicoidal phase mask, is strongly resistant against beam aberrations and therefore the helicoidal phase mask is widely used in STED, especially in thick samples. On the downside, however, the helicoidal phase mask creates a toroidal depletion-focus, that results in a highly anisotropic effective PSF that is confined in the lateral (xy) plane but still diffraction-limited in the axial (z) direction. Consequently these STED images are superresolved in the lateral direction, but not along the optic axis. To image the intrinsic 3D organization of tissue at the finest detail, STED microscopy must exhibit 3D resolution enhancement.

For thin samples, two 3D STED methods have been demonstrated thus far. The highest resolution has been achieved with a complex setup utilizing two opposing objective lenses which is not compatible with thick sample geometries. Alternatively, using a single objective, an annular phase filter featuring a central circle with a phase step of $\pi$ radians ($\lambda/2$) has been applied. This phase mask creates a ring-shaped focus with additional high-intensity lobes above and below the central minimum and thereby allows suppression of fluorescence emission in all directions around the center. Unfortunately, this approach is far more susceptible to aberrations than the helicoidal phase mask approach and, not surprisingly, no 3D STED imaging has been demonstrated to date in thick samples.

One approach to avoiding aberrations is to embed the sample, for example tissue, in a refractive index-matching medium, but this approach is not compatible with living specimens.

One known approach to STED imaging is that proposed in E. Auksorius, B. R. Boruah, C. Dunsby, P. M. Lanigan, G. Kennedy, M. A. Neil, and P. M. French, "Stimulated emission depletion microscopy with a supercontinuum source and fluorescence lifetime imaging," Opt. Lett. 33, 113-115 (2008). In this document, a spatial light modulator (SLM) is used to modulate the phase of the STED beam. Holograms are written to the SLM to generate phase distributions in the +1 diffracted order—the flexibility of the SLM allows the generation of either a type I helical phase distribution or a type II distribution with a central disc phase shifted by $\pi$.

Although this document suggests that aberration correction may be possible using the programmable SLM the method used cites a paper which involves a direct measurement of the focus, i.e. a direct image of the STED beam focus. This is impracticable for real samples—for many samples, including biological samples, the aberrations are complex and this creates a difficulty for the correction of such aberrations.

Previously published sensorless adaptive optics (AO) microscopes of other types, such as confocal or two-photon microscopes, have used simple image quality metrics, such as total image brightness (sum of pixel values). The response of these metrics to suitably chosen aberration modes provided a well-defined maximum, which was typically quadratic, thus optimization could be readily performed using simple algorithms.

However, in the STED microscope, these simple metrics are of limited use. A heavily aberrated STED microscope does not effectively confine the fluorescence to a narrow region, but permits emission from fluorophores across a larger volume. If from this state the aberrations are corrected, there is an inherent drop in total image intensity as the depletion becomes more effective and the effective PSF encompasses fewer fluorophores. In other words, the optimum correction cannot be targeted by a simple metric such as image brightness.

An alternative approach uses relatively simple adjustments, such as an adjustment of the objective lens correction collar. Such a relatively simple static method cannot correct the complex aberrations that are actually encountered in STED microscopy.

A further need is to align the excitation and depletion beams in a STED microscope.

SUMMARY OF INVENTION

According to a first aspect of the invention there is provided a method of stimulated emission depletion microscopy including:
  a) capturing a fluoresence image from a stimulated emission depletion microscope having an excitation light path and a first light modulator in a depletion light path;
  b) calculating a metric combining a measure of image brightness and a measure of image sharpness of the fluoresence image;
  c) adjusting a pattern on the first light modulator; and repeating (a), (b) and (c) to reduce optical aberrations and/or to align the depletion light path and in the excitation light path by maximising or minimising the metric, wherein the light modulator is a spatial light modulator or a deformable mirror.

The method according to this aspect uses a novel image quality feedback metric and demonstrates resolution well below the diffraction limit in all three dimensions when imaging through optically aberrating specimens such as tissue.

In another aspect there is provided a method of stimulated emission depletion microscopy comprising:

forming synchronised depletion and excitation beams, the depletion beam having a longer wavelength than the excitation beam;

directing the excitation beam along the excitation light path through an objective onto a sample and generating fluorescence;

directing the depletion beam onto a depletion light modulator and directing the depletion beam from the depletion light modulator through the objective onto the sample to form a depletion beam with a point spread function having a minimum value at a center to de-excite the fluorescence away from the center;

capturing the fluoresence from the center;

moving the center relative to the sample to a plurality of positions to build up a fluoresence image;

determining a metric of the fluoresence image including a measure of image brightness and a measure of image sharpness; and adapting the pattern on the depletion light modulator to reduce optical aberrations by maximising or minimising the metric.

In another aspect, there is provided a method of stimulated emission depletion microscopy including:

a) capturing a fluoresence image from a stimulated emission depletion microscope having an excitation light path and a first light modulator in a depletion light path;

(b) repeating (a) using a different pattern on the first light modulator to have a different enhancement effect; and combining the fluoresence images.

BRIEF DESCRIPTION OF DRAWINGS

Embodiments of the invention will be disclosed, purely by way of example, with reference to the accompanying drawings in which.

DETAILED DESCRIPTION

Figure 1:
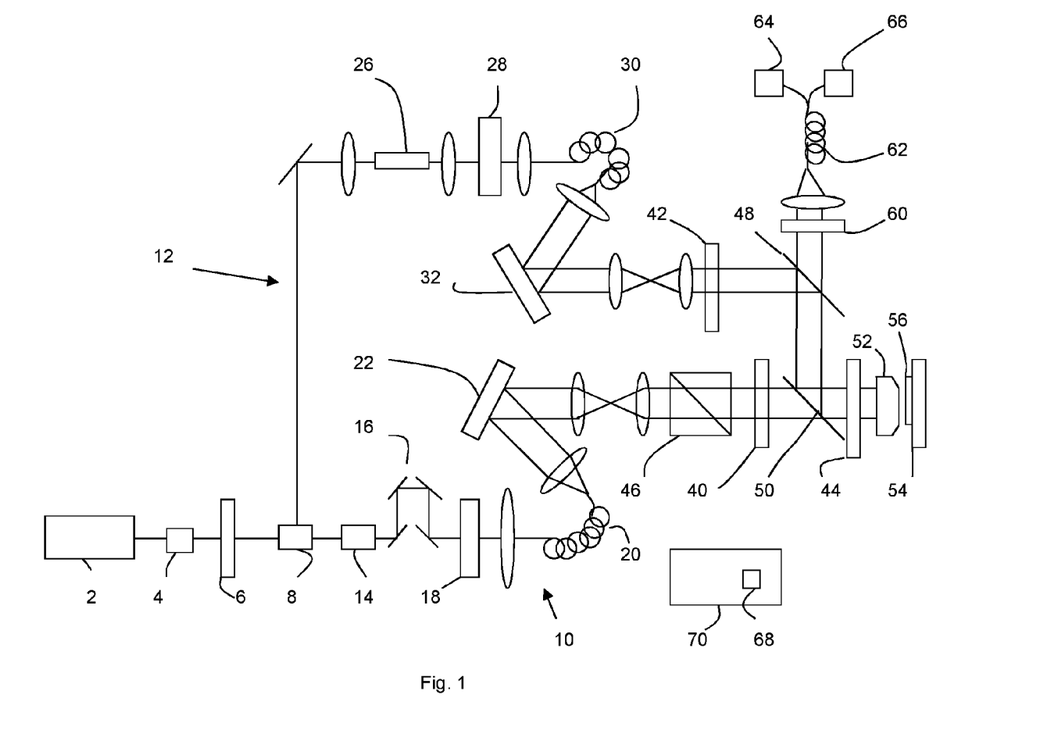
FIG. 1 shows a schematic of an embodiment of the invention.

FIG. 1 illustrates the AO STED setup used in an example embodiment. The output from an 80 MHz mode-locked Ti:Sapphire laser 2 was passed through a Faraday isolator 4 and a half-wave plate 6 before being split into two beam paths 10,12 by a Glan laser polarizer 8. The transmitted beam 10 was used for STED illumination, i.e. for depletion, and hence the corresponding optical path will be referred to as the depletion pulse beam path 10. This beam was passed through a 19 cm long glass block 14, a delay stage 16 for pulse delay adjustment, and an acousto-optical modulator 18 for laser power adjustment before it was coupled into a 100 m long polarization-maintaining single mode fiber 20. The glass block and single mode fiber served to stretch the pulses to a few hundred picoseconds.

To generate synchronized excitation pulses, the excitation beam along excitation beam path 12 reflected at the Glan laser polarizer was focused into a photonic crystal fiber 26 (SCG-800, Newport—®). The white light spectrum output from this fiber 26 was coupled to an acousto-optical tunable filter 28 for wavelength selection and power control and then coupled into a second polarization-maintaining single mode fiber 30.

At the output of each single mode fiber 20,30, the beams 10,12 were collimated and reflected off of a respective liquid crystal spatial light modulator 22,32 (SLM) placed in a plane conjugate to the objective pupil.

Half-wave plates 40, 42 in each beam path and a quarter-wave plate 44 in the common beam path were used to produce circular polarization of each beam in the sample. Additionally, a polarizing beam splitter cube 46 was used in the depletion beam path to clean up the beam polarization.

The beams were merged to a common path by a dichroic mirror 50 before being focused by a 100×/1.4NA oil immersion objective lens 52 (UPLSAPO 100XO/PSF, Olympus) mounted in a commercial microscope stand (IX71, Olympus). Samples 56 were mounted to an xyz piezo stage 54 (PINano, Physik Instrumente) for scanning. The fluorescence signal was collected by the objective, separated from the incoming beam paths 10,12 by dichroic mirrors 48,50, filtered by two bandpass filters 60, and focused into a 62.5 µm core diameter (~0.64 Airy units) 50:50 signal-splitting multimode fiber 62. Each output of the multimode fiber 62 was attached to a single photon counting avalanche photodiode 64,66. Image acquisition and instrument control was achieved using instrument PC 70 using software 68.

For imaging, the Ti:Sapphire laser 2 was tuned to 770 nm for depletion and an excitation line at 633 nm was selected from the output of the photonic crystal fiber 26 using the AOTF 28. Laser powers measured at the objective back aperture were 84-132 mW and 0.2-2 µW for depletion and excitation, respectively.

Images (128×128 pixels) were acquired with a scan rate of 100 lines/s, a pixel size of 40 nm, and 1-3 frame accumulations (corresponding to 1.28-3.84 s/image). Lines were scanned unidirectionally using a sinusoidal velocity profile which resulted in a pixel dwell time of 21.5 µs at the scan center and approximately twice this value at the edges. Recorded pixel values were therefore normalized according the pixel dwell times such that the center pixel was divided by unity. Fitting of line profiles was performed either using a Lorentzian (for images taken after aberration correction) or a Gaussian function (for images taken without aberration correction since in this case the observed data did not fit a Lorentzian profile).

The STED phase mask as well as aberration correction were realized using the SLM 22 placed in the depletion beam path. The 800×600 pixels of the SLM 22 were addressed individually by connecting the SLM as an additional display device to the instrument PC 70.

Phase modulation from 0 to $2\pi$ radians (and more) at the wavelengths used is achieved by varying the gray scale of the phase image fed to the SLM 22. Phase modulations significantly larger than $2\pi$ radians can be produced through phase-wrapping, whereby larger phase values are translated into the range 0 to $2\pi$ radians. Although aberrations affect the illumination, emission and depletion beam paths, the achievable resolution is dominated by the quality of the depletion focus.

For this reason, aberration correction by the SLM 22 solely in the depletion path 10 is sufficient to significantly improve the image quality.

Aberrations in the illumination and emission paths, however, influence the level of fluorescence excitation (by reducing the illumination intensity in the focus), the detection efficiency (by blurring the fluorescence focus on the confocal pinhole) and the background signal (through excitation and detection of fluorescence outside of the depletion region). Therefore, a second SLM 32 was included to perform additional aberration correction in the excitation beam path 12.

In an alternative embodiment, further improvement may be attained with aberration correction in the emission path as well.

Instead of using a direct reflection in SLM 22,32 an off-axis hologram was used which directs a non-zero order diffracted beam, here a first order beam, forward through the objective. The use of such a diffracted beam is beneficial because it separates the phase-modulated light from any directly reflected, unmodulated light.

In the arrangement described an active pupil was defined on the SLM 22 by creating such an off-axis hologram (FIG. 1 insets)—a blazed grating of circular outline that diffracts light off the principal reflection axis into the first diffraction order—and the diffracted light was focused into the sample. The remaining small non-diffracted fraction of the incident light (as well as light reflected from parts outside the active pupil) were simply reflected along the principal reflection axis and formed a secondary focus in the sample, much weaker than the depletion spot, approximately 3 μm away from the primary focus. This approach ensured that any residual light stemming from imperfect phase modulation could not interfere with the desired depletion focus and reduce its quality.

We note that the non-diffracted light could also be blocked at an intermediate focal plane if necessary. Phase masks for creating the depletion focus were produced by adding the corresponding function to the SLM phase pattern. In this manner, phase masks can be added, modified and exchanged with considerable ease, compared to systems where manufactured phase plates are physically placed in the optical path.

The microscope employed an oil immersion lens 52 of numerical aperture (NA) 1.4. Specimens were mounted in either aqueous media (phosphate buffered saline, PBS) of refractive index n=1.34 or glycerol (n=1.47). For the aqueous mounting media, the limiting system NA is restricted to the refractive index of the mounting medium due to total internal reflection at higher angles of incidence of the focusing beam. We therefore restricted the active aperture defined on the SLM to a size corresponding to an objective NA of 1.325. This enabled us, in effect, to mimic the performance of a water immersion objective lens of NA=1.325, which is higher than commercially available objectives.

The SLM enables adaptive aberration correction through the addition of further phase functions to the SLM. In the system described here we employed a sensorless AO scheme to determine the aberrations induced by the system and specimen. In sensorless AO, aberrations are estimated through analysis of a set of images that is obtained using a sequence of predetermined bias aberrations. This process requires 1) expansion of the aberrations using an appropriate set of modes, and 2) definition of an image quality metric that is maximized to find the optimal aberration correction.

Aberrations were represented using a Zernike polynomial expansion modified to remove small image shifts introduced by displacement (tip, tilt, and defocus) modes. Table 1 lists the Zernike modes (following a conventional numbering used for aberration correction in this work. Zernike polynomial modes are widely used to model aberrations in adaptive optics. One reason for this is the orthogonality between the modes, which has useful practical consequences, such as the separation of displacement of the focus (by tip, tilt and defocus modes) and distortion of the focus (through higher order modes such as astigmatism, coma and spherical aberration). However, this separation of effects is only strictly true in the paraxial approximation and with a uniform pupil function.

Those skilled in the art will realise that alternative modes may be used to represent aberrations and the method will work with such alternative modes.

When using phase masks and high NA lenses in STED microscopy, these approximations are no longer valid. We observed experimentally that the zero intensity point of the depletion focus can shift laterally when, for example, Zernike coma is applied using the SLM. Similar axial shifts were observed when applying Zernike spherical modes. This behavior has been confirmed through theoretical modeling (data not shown). In order to remove these displacement effects, we measured the induced focal shifts for each Zernike mode using images of gold beads. Using a linear approximation of the zero shift, a proportionate amount of the tip, tilt, or defocus mode (as appropriate) was added to each applied Zernike mode to ensure that the intensity zero did not shift position. This procedure defined a modified set of "displacement-free" Zernike modes that was used for the subsequent experiments. Subsequent references to Zernike modes will hereafter represent displacement-free Zernike modes.

TABLE 1

Definition of Zernike Modes, $Z_i$.

| i | Aberration | $Z_i$ (r, θ) |
|---|---|---|
| 2 | Tip | $2r\cos(\theta)$ |
| 3 | Tilt | $2r\sin(\theta)$ |
| 4 | Defocus | $\sqrt{3}(2r^2 - 1)$ |
| 5 | Astigmatism | $\sqrt{6}r^2\cos(2\theta)$ |
| 6 | Astigmatism | $\sqrt{6}r^2\sin(2\theta)$ |
| 7 | Coma | $2\sqrt{2}(3r^3 - 2r)\cos(\theta)$ |
| 8 | Coma | $2\sqrt{2}(3r^3 - 2r)\sin(\theta)$ |
| 9 | Trefoil | $2\sqrt{2}r^3\cos(3\theta)$ |
| 10 | Trefoil | $2\sqrt{2}r^3\sin(3\theta)$ |
| 11 | $1^{st}$ Spherical | $\sqrt{5}(6r^4 - 6r^2 + 1)$ |
| 22 | $2^{nd}$ Spherical | $\sqrt{7}(20r^6 - 30r^4 + 12r^2 - 1)$ |
| 37 | $3^{rd}$ Spherical | $3(70r^8 - 140r^6 + 90r^4 - 20r^2 + 1)$ |

Figure 2:
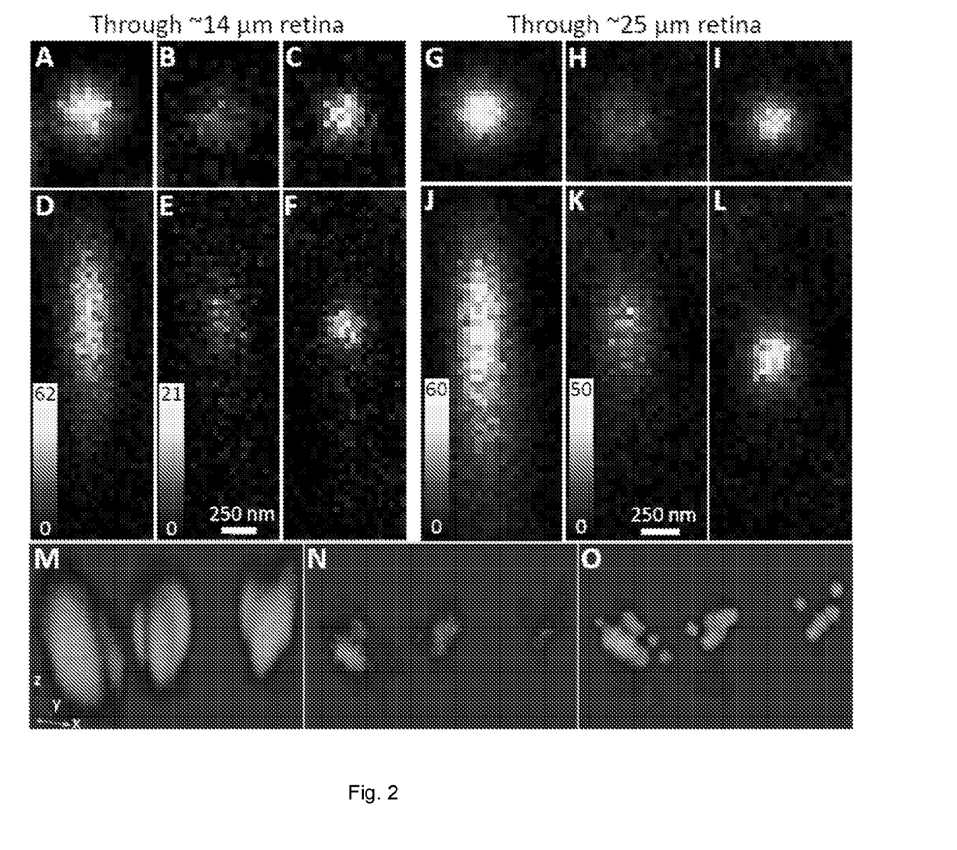
FIG. 2 shows images corrected using an embodiment of the invention.

The inventors have observed that close to the optimum correction the adjustment of certain aberration modes caused a decrease in image intensity, whereas others led to an increase (FIG. 2). The brightness metric alone is therefore inappropriate in the STED microscope.

Metrics related to image sharpness might in principle seem better suited, but optimization purely on this basis is susceptible to degradation of the STED focus as the metric is misled by the background noise (noise tends to be "sharper" than the imaged specimen). It was further found that the response of the sharpness metric to some aberration modes was very flat near optimum correction, exhibiting a variation that was closer to quartic than quadratic.

In practice, the characteristics that we desire from a STED image are high brightness combined with high resolution. The metric used seeks to optimize both image brightness and image sharpness in a combined approach, which succeeds where either separate approach can fail.

In one embodiment, the combined metric was defined as $$M = S + \sigma\beta B\left[\frac{1}{1+e^{-k(S-S_T)}}\right] \quad (1)$$

where B and S are brightness and sharpness metrics, respectively. The expression in brackets in Eq. 1 is a logistic function that, in effect, introduces the contribution of the brightness metric B only when the sharpness metric S is above a particular threshold $S_T$ (typically chosen to be 90% of the peak sharpness). The parameter β was chosen empirically to balance the contributions from S and B and the parameter k was used to adjust the rate of transition of the logistic function in the region of $S \approx S_T$. The constant σ was +1 or −1 dependent upon whether the aberration mode in question produced a minimum or maximum in B for zero aberration magnitude.

In more general terms, the metric M combines sharpness and brightness. In embodiments, the metric M can alternatively be expressed as:

$$M = S + \sigma\beta Bf(S) \quad (2)$$

where f(S) is a function of S that has a higher absolute value for S above $S_T$ and a lower absolute value for S below $S_T$.

The image brightness metric B was calculated as the sum of the pixel values in the confocal or STED image. This image brightness metric B was used alone as the metric for the adjustment of the excitation beam path 12, i.e. as a second metric B used for aberration correction using the SLM 32 in the excitation beam path.

The sharpness metric S was defined as the second moment of the image Fourier transform (FT) and calculated as $$S = \sum_{n,m} \mu_{n,m} \hat{I}_{n,m}(n'^2 + m'^2) \Big/ \sum_{n,m} \hat{I}_{n,m} \quad (3)$$

where $\hat{I}_{n,m}$ is the discrete FT of the image, $$n' = n - \frac{N-1}{2}, \ m' = m - \frac{M-1}{2},$$

and n and m are the coordinates ranging from 0 to N−1 or M−1, respectively. The function $\mu_{n,m}$ is a circular mask defined by:

$$\mu_{n,m} = \begin{cases} 1 & \sqrt{n'^2 + m'^2} \leq w \\ 0 & \sqrt{n'^2 + m'^2} > w \end{cases} \quad (4)$$

where w is a radius (in units of pixels of the image FT) defined as the size of the field of view divided by an upper bound on the expected resolution (for example 200 nm).

This mask is used to cut off higher spatial frequencies that would otherwise cause S to be dominated by noise. The motivation for this choice of metric lies in the inverse relationship between the width of image features and the width of the corresponding image's spatial frequency spectrum—sharp images lead to a broad image FT. As the second moment calculation of Eq. 3 is a measure of width of the image FT, it follows that a large value of S corresponds to a sharp image arising from a narrow PSF. The definition of M should mean that it is readily applicable to any sample that features structures smaller than the diffraction limit.

It is important to note that the 2nd and 3rd spherical modes lead to decreases in image brightness while the 1st spherical mode leads to a brightness increase when imaging with the central λ/2 phase mask. These results reveal that manual adjustment of the objective correction collar to maximize image brightness cannot necessarily be applied to 3D STED microscopy as the collar adjusts a combination of these spherical aberration modes.

For the sensorless adaptive optics scheme of this embodiment, images (single accumulation) were acquired in either confocal (for excitation path correction) or STED (for depletion path correction) mode while adding a bias aberration, $bZ'_i$, of a given mode $Z'_i$ where b was a suitably chosen bias amplitude. Typically, b was chosen to cover the range of −1 to +1 radian while acquiring a number of images for each Zi. For each image the appropriate metric was calculated (B for excitation path correction; M for depletion path correction) and then plotted as a function of the bias amplitude b. The correction aberration, $a_{corr}$, was then estimated as the peak of the curve, which was calculated by fitting a quadratic function to the data. In cases where a quadratic approximation did not represent the data, peaks could be identified manually.

The aberration $a_{corr}Z'_i$ was then added to the SLM phase pattern, and this measurement and correction cycle was then repeated for each of the modes of interest.

Aberrations due to coma, astigmatism, and trefoil could be assessed using a single iteration of our correction routine. Spherical modes were typically the dominant aberrations in the experiments conducted here and typically required 1-4 correction iterations to converge to optimal values. However, when results for correcting the excitation beam path were used as a starting point for correction of the depletion beam path 1-2 iterations were typically sufficient to assess the spherical aberrations. All AO STED images shown are of the same field of view used to perform aberration correction.

To test the correction procedure using aberrations encountered in biological specimens, 200 nm crimson beads were added on top of zebrafish retina sections attached to #1.5 coverglass and then mounted in PBS (to mimic the aqueous embedding conditions of live sample imaging) onto a microscope slide. FIGS. 2A-L show xy and xz images of an individual bead after focusing ~14 μm or ~25 μm through the retina sections.

Images A, D, G. J and M show a confocal image, i.e. without the use of the depletion beam path at all. Images B, E, H, K and N show the improvement in resolution using STED, i.e. with the depletion beam path. Images C, F, I, L and O show the improvement using aberration correction in the depletion beam path 10 using SLM 22.

In this example all aberration correction was performed solely on the depletion beam path 10 to demonstrate that correction of the depletion beam path is possible without prior knowledge of corrections made to the excitation path 10. These data also demonstrate that the quality of the depletion focus is the dominating factor in achieving sub-diffraction resolution in the STED images. While correction of relatively few aberration modes was sufficient to obtain ~200 nm and ~250 nm axial resolution for imaging depths of ~14 μm and ~25 μm, respectively, we expect that including higher order aberrations in the correction routine should further improve the STED resolution. FIGS. 2M-O show volume renderings of the data depicted in FIGS. 2A-F and represent the first 3D super-resolution STED image recorded through scattering tissue.

To demonstrate correction of aberrations induced by a strongly aberrating sample, using both beam paths 10,12, the inventors also imaged fluorescent beads through a layer of glycerol (n=1.47). Samples with fluorescent beads were prepared by attaching 100 nm crimson beads to the microscope slide coated with poly-L-lysine and beads were imaged through a #1.5 coverglass and ~55 μm of glycerol which was used as the embedding medium.

Figure 3:
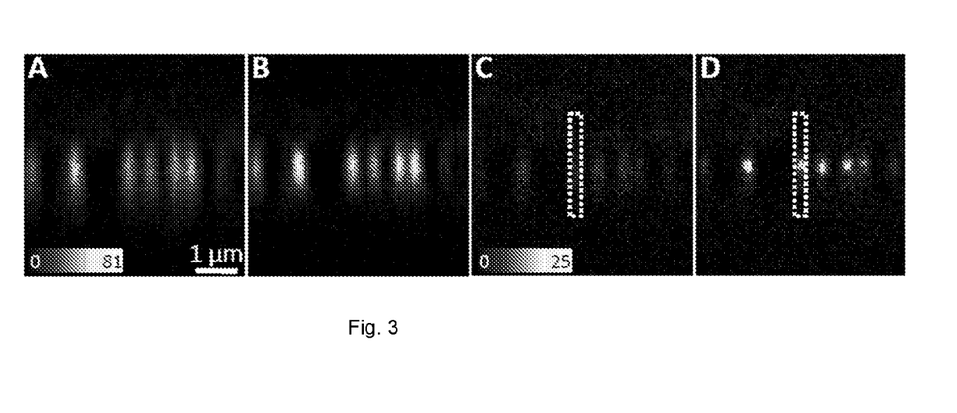
FIG. 3 shows images corrected using an embodiment of the invention.

FIG. 3 shows the bead images before and after aberration correction in regular confocal and in STED imaging modes. In FIG. 3, image A shows the image in confocal mode without STED, image B shows image A with the correction of the sample induced aberrations in the excitation beam path 12 only using SLM 32 and the second metric B, still without STED. Image C shows the image using STED but only correcting the excitation beam path 12 using SLM 32, i.e. as image B but with STED. Image D shows the result of correcting for aberrations in both depletion 10 and excitation 12 beam paths.

The aberration correction routine began by correcting the excitation beam path 12 using the image brightness B alone as the metric in confocal imaging mode and adjusting SLM 32.

The resulting correction values were then used as the starting point for correction of the depletion beam path 10 using the combined metric defined in Eq. 1 in STED imaging mode. FIGS. 3A and B illustrate the benefits of using a second SLM to correct aberrations in the excitation beam path (for confocal imaging). As shown in FIG. 3C, the non-corrected STED image exhibits moderately improved resolution compared to the confocal image, but at the expense of a significant decrease in the signal level as the non-zero central intensity depletes the fluorescence. On the other hand, correction of aberrations significantly enhances both the intensity and resolution of the STED image (FIG. 3D).

Figure 4:
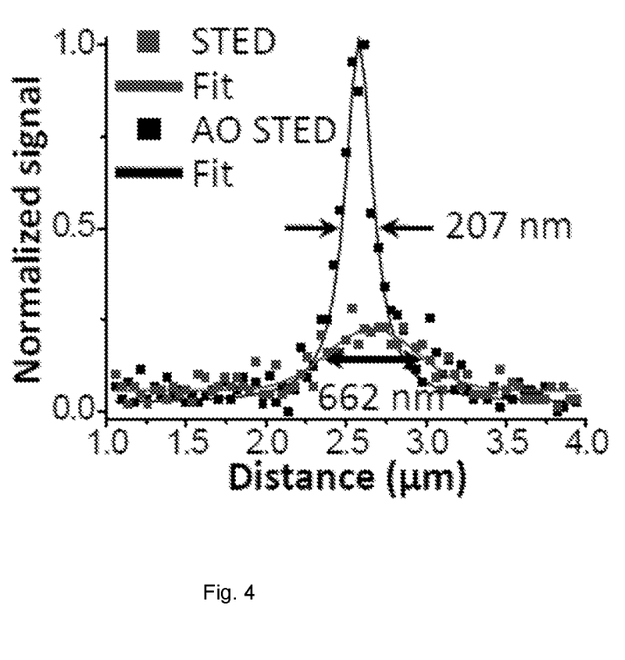
FIG. 4 shows the improvement with the adaptive optics approach of an embodiment of the invention.

The axial profiles of the STED and AO STED images were plotted for comparison (FIG. 4) and the results show a ~5-fold increase in the peak signal as well as a ~3.2-fold improvement in resolution.

We note that the STED images shown in FIGS. 2 and 3 before and after aberration correction are of the same beads on which the correction routine was performed, thus demonstrating that photobleaching was not significant in these experiments. Labeling conditions in biological imaging applications are likely to use less photostable fluorophores, which in some instances may not tolerate the acquisition of 5-7 STED images per aberration mode. However, it has been demonstrated that only 2N+1 images are required to correct for N aberration modes and we expect this approach to be compatible with methods presented here. Furthermore, applications otherwise inhibited by photobleaching may benefit from the implementation of triplet-state-relaxation during STED imaging either by increasing scan rates or using lower repetition rate lasers.

The set up proposed can also be used for automatic alignment. In particular, to align the excitation light path with the depletion light path, the pattern on the depletion beam path light modulator is adjusted by adding an amount of a beam mode, such as tip or tilt, to the light modulator and then acquiring an image. A suitable metric is calculated and optimised to align the excitation and depletion paths.

In the same manner as used for aberration correction, the correct choice of metric is important in the case of automatic beam alignment. Close to optimum alignment, the STED images will be maximally bright when the position of the intensity zero is aligned to the center of the Gaussian focus of the excitation focus. Unfortunately, further from optimum alignment, non overlapping beams result in a conventional confocal image also of high brightness. Accordingly, a simple metric based on brightness is not suitable.

Therefore, in order to correct for beam misalignment, a metric M combining brightness and sharpness is used in a coarse alignment step. This is followed by a fine alignment step using simply a metric related to brightness B.

Note that a particular benefit of the proposed approach is that the correction of optical aberrations and the coarse alignment may both use the metric M and so may be carried out as a single operation, i.e. a single optimisation approach may both align and correct for aberrations.

In the paper by Auksorius referenced above report an SLM was reported to be used to correct for system aberrations in the depletion beam path through direct observation of the depletion focus. However, this method is not practical for correction of aberrations introduced in microscopy of real specimens, where one usually has access only to the fluorescence images. The present invention permits aberration correction using the super resolution image itself, which is a significant step towards making automated AO practical for biological superresolution microscopy.

The SLM provides a convenient way to combine a STED phase mask and adaptive aberration correction in the same microscope.

The skilled person will realise that modifications may be made to the embodiments described above.

The embodiment described above uses SLMs in both depletion path and excitation path. In some embodiments, an SLM is provided only in the depletion path. In other embodiments, a light modulator may be provided in the fluoresence emission and detection path between the sample and the detector.

There are alternatives to the use of SLMs as light modulators. For example, deformable mirrors could be used instead of the SLM as a light modulator. The alternative approach of using deformable mirrors would have the advantage of being able to correct all three (depletion, excitation, and emission) beam paths with the same device. However, unlike the SLM, the continuous reflective surface of mirror devices does not permit the generation of the STED phase masks, which require discontinuous phase jumps.

A further approach is to use a light modulator at a location where the beam paths coincide to allow multiple beam paths to be corrected using a single light modulator.

Figure 5:
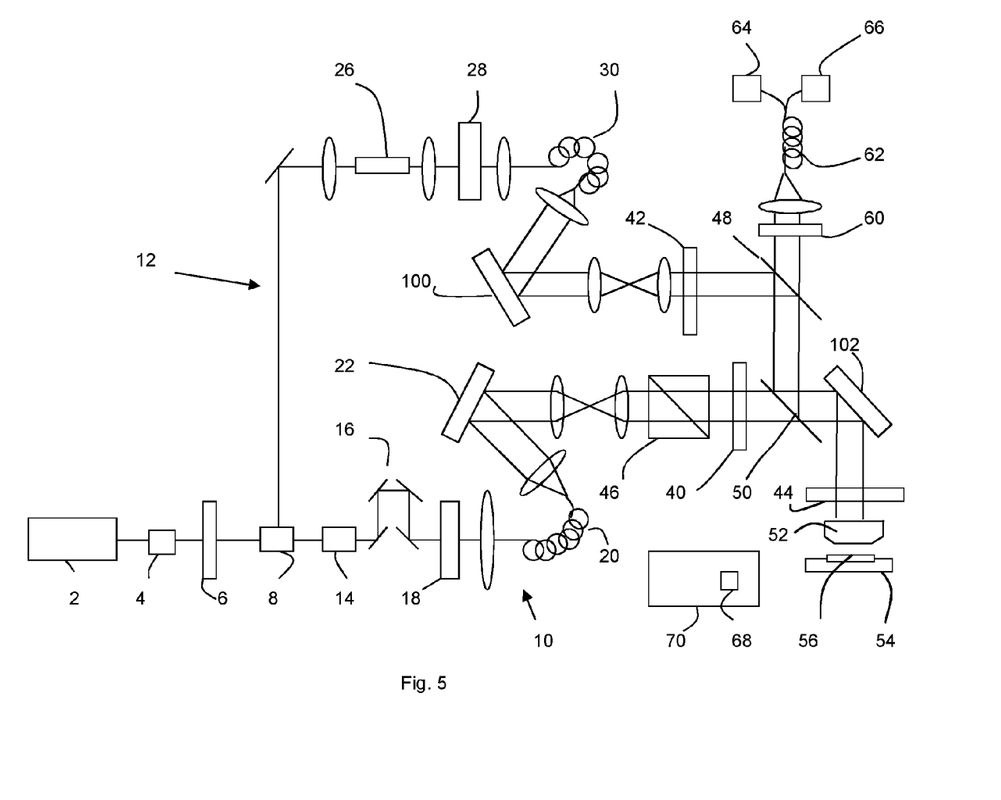
FIG. 5 is schematic and not to scale.

An alternative embodiment illustrating these options is FIG. 5. In this embodiment, there are two light modulators. One of these is the depletion beam path SLM 22 located in the depletion path alone and the second light modulator is a combined beam path deformable mirror 102 located where the three beam paths coincide. Note that the SLM 32 in the excitation path in FIG. 1 is replaced by a simple mirror 100.

In this approach, the depletion beam path SLM 22 is used to correct the phase pattern to shape the depletion focus and to provide abberation correction. The second light modulator, i.e. the deformable mirror 102 is used to correct each of the depletion path, excitation path and emission path.

Those skilled in the art will realise that light modulators may be provided in each of the depletion path, excitation path and emission path or shared as in the embodiment of FIG. 5.

Alternative sample mounting arrangements and ways of arranging optical components to direct light along the respective beam paths may be used as known in the art.

The invention claimed is:

1. A method of stimulated emission depletion microscopy using adaptive optics comprising:
    (a) capturing a fluorescence image from a stimulated emission depletion microscope having an excitation light path and a first light modulator in a depletion light path defining a pattern on the first light modulator, wherein the first light modulator is a spatial light modulator or a deformable mirror;
    (b) calculating a measure of image sharpness of the fluorescence image,
    calculating a measure of image brightness of the fluorescence image, and
    calculating a metric combining the measure of image brightness and the measure of image sharpness;
    wherein the metric M is defined by $$M=S+\sigma\beta Bf(S) \qquad (2)$$

wherein M is the metric, S an image sharpness measure, B an image brightness measure, σ is constant that has a value −1 or 1 depending on whether the aberration mode being corrected produces a maximum or minimum brightness, β is a constant and f(S) is a function of S that has a larger absolute value for a value of S above a threshold value $S_T$ and a lower absolute value for a value of S below the threshold value $S_T$:
    (c) adjusting the pattern on the first light modulator; and
    repeating (a), (b) and (c) to maximise or minimise the metric combining the measure of image brightness and the measure of image sharpness.

2. A method of stimulated emission depletion microscopy according to claim 1 wherein (a) capturing the fluorescence image comprises:
    forming synchronised depletion and excitation beams, the depletion beam having a longer wavelength than the excitation beam;
    directing the excitation beam along the excitation light path through an objective onto a sample and generating fluorescence;
    directing the depletion beam along the depletion light path onto a depletion light modulator and directing the depletion beam from the depletion light modulator through the objective onto the sample to form a depletion beam with a point spread function having a minimum value at a center to de-excite the fluorescence away from the center;
    capturing the fluorescence from the center;
    moving the center relative to the sample to a plurality of positions to build up the fluorescence image.

3. A method according to claim 2, wherein the method further comprises:
    directing the excitation beam onto an excitation light modulator and directing the excitation beam from the excitation light modulator through the objective onto the sample to generate fluorescence; and
    adapting the pattern on the excitation light modulator to reduce optical aberrations by maximising or minimising the image brightness measure B.

4. A method according to claim 2, wherein the path from the sample to the detector is an emission light path, the method further comprising:
    directing the light from the sample through the objective onto a second light modulator and then onto the detector; and
    adapting the pattern on the second light modulator to reduce optical aberrations by maximising or minimising a further metric being a measure of image brightness.

5. A method according to claim 4 wherein the second light modulator is also in the excitation light path and wherein:
    adapting the pattern on the second light modulator to reduce optical aberrations by maximising or minimising a further metric includes adapting the pattern on the second light modulator to reduce optical aberrations in both the excitation light path and the emission light path.

6. A method according to claim 5 wherein the second light modulator is in the depletion light path as well as the emission light path and the excitation light path and wherein:
    adapting the pattern on the second light modulator to reduce optical aberrations by maximising or minimising a further metric includes adapting the pattern on the second light modulator to reduce optical aberrations in each of the depletion light path, the excitation light path and the emission light path.

7. A method according to claim 1 including correcting for a plurality of optical aberration modes.

8. A method according to claim 2 wherein the pattern on the depletion light modulator is a pattern arranged to direct a non-zero order diffraction peak onto a sample as the depletion beam with a point spread function.

9. A method according to claim 1 wherein the metric M is defined by $$M = S + \sigma\beta B\left[\frac{1}{1+e^{-k(S-S_T)}}\right] \qquad (1)$$

where k is a constant of proportionality.

10. A method according to claim 1 wherein the measure of image brightness B is calculated as the sum of the pixel values in the image.

11. A method according to claim 1 wherein the measure of image sharpness S is defined as the second moment of the image Fourier transform (FT) and calculated as $$S = \sum_{n,m} \mu_{n,m}\hat{i}_{n,m}(n'^2 + m'^2) \Big/ \sum_{n,m} \hat{i}_{n,m} \qquad (3)$$

where $\hat{i}_{n,m}$ is the discrete FT of the image, $$n' = n - \frac{N-1}{2}, m' = m - \frac{M-1}{2},$$

and n and m are the coordinates ranging from 0 to N−1 or M−1, respectively, wherein the function $\mu_{n,m}$ is a circular mask defined by:

$$\mu_{n,m} = \begin{cases} 1 & \sqrt{n'^2 + m'^2} \le w \\ 0 & \sqrt{n'^2 + m'^2} > w \end{cases} \quad (4)$$

12. A method according to claim 1 further comprising:
carrying out a fine adjustment procedure to provide a fine alignment of one or more of the depletion light beam, the excitation light beam and the emission beam path by repeating the steps:
(d) capturing a fluorescence image from the stimulated emission depletion microscope;
(e) calculating a metric measuring image brightness, image sharpness of the fluorescence image or both; and
(f) adjusting a pattern on the light modulator.

13. A computer program product, that is arranged:
(a) to capture a fluorescence image from a stimulated emission depletion microscope having an excitation beam along an excitation path and a spatial light modulator in the depletion optical path of a depletion beam defining a pattern on the first light modulator wherein the first light modulator is a spatial light modulator or a deformable mirror;
(b) to calculate a measure of image sharpness of the fluorescence image,
calculate a measure of image brightness of the fluorescence image, and
calculate a metric, the metric combining the measure of image brightness and the measure of image sharpness of the fluorescence image wherein the metric M is defined by $$M = S + \sigma\beta Bf(S) \quad (2)$$

wherein M is the metric, S an image sharpness measure, B an image brightness measure, σ is constant that has a value −1 or 1 depending on whether the aberration mode being corrected produces a maximum or minimum brightness, β is a constant and f(S) is a function of S that has a larger absolute value for a value of S above a threshold value $S_T$ and a lower absolute value for a value of S below the threshold value $S_T$:
(c) to adjust the pattern on the spatial light modulator; and
to repeat (a), (b) and (c) to maximise or minimise the metric.

14. A computer program product according to claim 13 arranged to capture the captured image from the stimulated emission depletion microscope, the microscope further comprising a second spatial light modulator;
wherein the computer program product is arranged to adjust the pattern on both the first and the second spatial light modulator.

15. A computer program product according to claim 13 wherein the measure of image sharpness S is defined as the second moment of the image Fourier transform (FT) and calculated as $$S = \sum_{n,m} \mu_{n,m} \hat{I}_{n,m}(n'^2 + m'^2) \Big/ \sum_{n,m} \hat{I}_{n,m} \quad (3)$$

where $\hat{I}_{n,m}$ is the discrete FT of the image, $$n' = n - \frac{N-1}{2}, m' = m - \frac{M-1}{2},$$

and n and m are the coordinates ranging from 0 to N−1 or M−1, respectively, wherein the function $\mu_{n,m}$ is a circular mask defined by:

$$\mu_{n,m} = \begin{cases} 1 & \sqrt{n'^2 + m'^2} \le w \\ 0 & \sqrt{n'^2 + m'^2} > w \end{cases} \quad (4)$$

16. A stimulated emission depletion microscope, comprising:
a light source;
a splitter for splitting light from the light source into a depletion optical path and an excitation optical path;
an objective for directing the light passing through the excitation optical path onto a subject;
a frequency shifter for shifting the frequency of light travelling through the depletion optical path to a lower frequency;
a light modulator arranged to direct the light travelling through the depletion optical path through the objective onto the sample with a point spread function having a minimum value at a center to de-excite the fluorescence away from the center wherein a pattern is defined on the first light modulator, the first light modulator being a spatial light modulator or a deformable mirror;
a sensor for capturing fluorescent light from the center;
a controller for building up a fluorescence image of the sample from the sensed light at a plurality of centers, calculating a measure of image sharpness of the fluorescence image, calculating a measure of image brightness of the fluorescence image, and calculating a metric combining the measure of image brightness and the measure of image sharpness wherein the brightness measure is scaled down when the sharpness measure is lower; and adapting the pattern on the light modulator to maximise or minimise the metric,
wherein the metric M is defined by $$M = S + \sigma\beta Bf(S) \quad (2)$$

wherein M is the metric, S the measure of image sharpness, B the measure of image brightness, σ is constant that has a value −1 or 1 depending on whether the aberration mode being corrected produces a maximum or minimum brightness, β is a constant and f(S) is a function of S that has a larger absolute value for a value of S above a threshold value $S_T$ and a lower absolute value for a value of S below the threshold value $S_T$.

17. A stimulated emission depletion microscope according to claim 16, further comprising a second light modulator in the excitation optical path.

18. A stimulated emission depletion microscope according to claim 17, wherein the second light modulator is a deformable mirror in each of the depletion optical path, the excitation optical path, and an emission optical path, the emission optical path being the optical path between the sample and the sensor.

19. A stimulated emission depletion microscope according to claim 16 wherein the first light modulator is arranged to display a diffraction pattern to direct a non-zero order diffraction peak onto the sample with a point spread function.

* * * * *